United States Patent
Jonas et al.

(10) Patent No.: US 6,777,419 B1
(45) Date of Patent: Aug. 17, 2004

(54) PYRAZOLO [4,3-D]PYRIMIDINES

(75) Inventors: Rochus Jonas, Darmstadt (DE);
Hans-Michael Eggenweiler,
Weiterstadt (DE); Pierre Schelling,
Mühltal (DE); Maria Christadler,
Rödermark (DE); Norbert Beier,
Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/070,305

(22) PCT Filed: Aug. 24, 2000

(86) PCT No.: PCT/EP00/08257

§ 371 (c)(1),
(2), (4) Date: Jul. 29, 2002

(87) PCT Pub. No.: WO01/18004

PCT Pub. Date: Mar. 15, 2001

(30) Foreign Application Priority Data

Sep. 6, 1999 (DE) .......................................... 199 42 474

(51) Int. Cl.[7] ..................... C07D 487/04; A61K 31/519; A61P 9/04; A61P 15/10
(52) U.S. Cl. ..................................... 514/262.1; 544/262
(58) Field of Search ........................ 544/262; 514/262.1

(56) References Cited

U.S. PATENT DOCUMENTS 5,256,650 A * 10/1993 Peet et al. ................... 544/262
2004/0023990 A1 * 2/2004 Eggenweiler ............ 514/262.1
2004/0023991 A1 * 2/2004 Eggenweiler ............ 514/262.1
2004/0029900 A1 * 2/2004 Jonas et al. ............... 514/262.1
2004/0053945 A1 * 3/2004 Eggenweiler ............ 514/262.1

FOREIGN PATENT DOCUMENTS

WO     WO 98 49166     11/1998

OTHER PUBLICATIONS

International Search Report for International Application No. PCT/EP 00/08257.

* cited by examiner

*Primary Examiner*—Mark L. Berch
(74) *Attorney, Agent, or Firm*—Millen, White, Zelano & Branigan, P.C.

(57) ABSTRACT

Pyrazolo[4,3-d]pyrimidines of the formula I

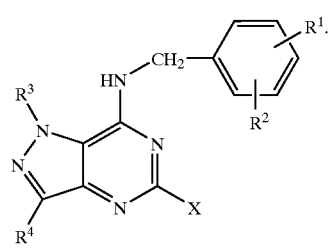

and their physiologically acceptable salts,
in which
$R^1$, $R^2$, $R^3$, $R^4$ and X have the meanings indicated in Claim 1, exhibit phosphodiesterase V inhibition and can be employed for the treatment of disorders of the cardiovascular system and for the treatment and/or therapy of potency disorders.

16 Claims, No Drawings

PYRAZOLO [4,3-D]PYRIMIDINES

The invention relates to compounds of the formula I

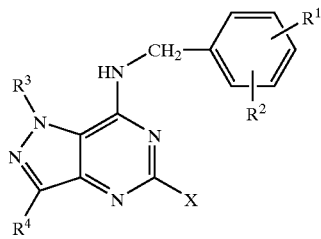

in which
  $R^1$, $R^2$ in each case independently of one another are H, A, OH, OA or Hal,
  $R^1$ and $R^2$ together are also alkylene having 3–5 C atoms, —O—CH$_2$—CH$_2$—, —CH$_2$—O—CH$_2$—, —O—CH$_2$—O— or —O—CH$_2$—CH$_2$—O—,
  $R^3$, $R^4$ in each case independently of one another are H or A,
  X is $R^5$, $R^6$ or $R^7$ monosubstituted by $R^8$,
  $R^5$ is linear or branched alkylene having 1–10 C atoms, in which one or two CH$_2$ groups can be replaced by —CH=CH— groups, O, S or SO,
  $R^6$ is cycloalkyl or cycloalkylalkylene having 5–12 C atoms,
  $R^7$ is phenyl or phenylmethyl,
  $R^8$ is COOH, COOA, CONH$_2$, CONHA, CON(A)$_2$ or CN,
  A is alkyl having 1 to 6 C atoms and
  Hal is F, Cl, Br or I,
and their physiologically acceptable salts and solvates.

Pyrimidine derivatives are disclosed, for example, in EP 201 188 and WO 93/06104.

The invention was based on the object of finding novel compounds having valuable properties, in particular those which can be used for the production of medicaments.

It has been found that the compounds of the formula I and their salts have very valuable pharmacological properties together with good tolerability.

In particular, they exhibit specific inhibition of cGMP phosphodiesterase (PDE V).

Quinazolines having cGMP phosphodiesterase-inhibiting activity are described, for example, in J. Med. Chem. 36, 3765 (1993) and ibid. 37, 2106 (1994).

The biological activity of the compounds of the formula I can be determined by methods such as are described, for example, in WO 93/06104. The affinity of the compounds according to the invention for cGMP and cAMP phosphodiesterase is determined by the determination of their IC$_{50}$ values (concentration of the inhibitor which is needed in order to achieve a 50% inhibition of the enzyme activity).

For carrying out the determinations, enzymes isolated according to known methods can be used (e.g. W. J. Thompson et al., Biochem. 1971, 10, 311). For carrying out the experiments, a modified batch method of W. J. Thompson and M. M. Appleman (Biochem. 1979, 18, 5228) can be used.

The compounds are therefore suitable for the treatment of disorders of the cardiovascular system, in particular of cardiac insufficiency, and for the treatment and/or therapy of potency disorders (erectile dysfunction).

The use of substituted pyrazolopyrimidinones for the treatment of impotence is described, for example, in WO 94/28902.

The compounds are efficacious as inhibitors of the phenylephrine-induced contractions in corpus cavernosum preparations from hares.

This biological action can be demonstrated, for example, according to the method which is described by F. Holmquist et al. in J. Urol., 150, 1310–1315 (1993). The inhibition of the contraction shows the efficacy of the compounds according to the invention for the therapy and/or treatment of potency disorders.

The compounds of the formula I can be employed as pharmaceutical active compounds in human and veterinary medicine. They can furthermore be employed as intermediates for the preparation of further pharmaceutical active compounds.

The invention accordingly relates to the compounds of the formula I and to a process for the preparation of compounds of the formula I according to Claim 1 and their salts, which is characterized in that
  a) a compound of the formula II

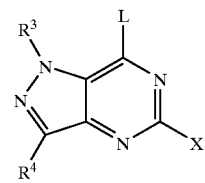

in which
  $R^3$, $R^4$ and X have the meanings indicated,
  and L is Cl, Br, OH, SCH$_3$ or a reactive esterified OH group,
  is reacted with a compound of the formula III

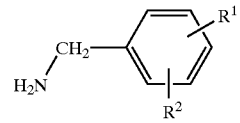

in which
  $R^1$ and $R^2$ have the meanings indicated, or
  b) in a compound of the formula I, a radical X is converted into another radical X by, for example, hydrolysing an ester group to a COOH group or converting a COOH group into an amide or into a cyano group
  and/or a compound of the formula I is converted into one of its salts.

Solvates of the compounds of the formula I are understood as meaning adducts of inert solvent molecules to the compounds of the formula I which are formed on account of their mutual attractive force. Solvates are, for example, mono- or dihydrates or alcoholates.

Above and below, the radicals $R^1$, $R^2$, $R^3$, $R^4$, $R^5$, $R^6$, $R^7$, $R^8$, X and L have the meanings indicated in the formulae I, II and III, if not expressly stated otherwise.

A is alkyl having 1–6 C atoms.

In the above formulae, alkyl is preferably unbranched and has 1, 2, 3, 4, 5 or 6 C atoms and is preferably methyl, ethyl or propyl, furthermore preferably isopropyl, butyl, isobutyl, sec-butyl or tert-butyl, but also n-pentyl, neopentyl, isopentyl or hexyl.

X is an $R^5$, $R^6$ or $R^7$ radical monosubstituted by $R^7$.

$R^5$ is a linear or branched alkylene radical having 1–10 C atoms, where the alkylene radical is preferably, for example, methylene, ethylene, propylene, isopropylene, butylene, isobutylene, sec-butylene, pentylene, 1-, 2- or 3-methylbutylene, 1,1-, 1,2- or 2,2-dimethylpropylene, 1-ethylpropylene, hexylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene, linear or branched heptylene, octylene, nonylene or decylene. $R^5$ is furthermore, for example, but-2-enylene or hex-3-enylene.

A $CH_2$ group in $R^5$ can preferably be replaced by oxygen. Ethylene, propylene, butylene or $CH_2$—O—$CH_2$ is very particularly preferred.

$R^6$ is cycloalkylalkylene having 5–12 C atoms, preferably, for example, cyclopentylmethylene, cyclohexylmethylene, cyclohexylethylene, cyclohexylpropylene or cyclohexylbutylene.

$R^6$ is also cycloalkyl preferably having 5–7 C atoms.

Cycloalkyl is, for example, cyclopentyl, cyclohexyl or cycloheptyl.

Hal is preferably F, Cl or Br, but also I.

The radicals $R^1$ and $R^2$ can be identical or different and are preferably in the 3 or 4 position of the phenyl ring. They are, for example, in each case independently of one another, H, alkyl, OH, F, Cl, Br or I or together alkylene, such as, for example, propylene, butylene or pentylene, furthermore ethylenoxy, methylenedioxy or ethylenedioxy. Preferably, they are also in each case alkoxy, such as, for example, methoxy, ethoxy or propoxy.

The radical $R^8$ is preferably, for example, COOH, COOA such as, for example, $COOCH_3$ or $COOC_2H_5$, $CONH_2$, $CON(CH_3)_2$, $CONHCH_3$ or CN, but in particular COOH or COOA.

It applies to the entire invention that all radicals which occur a number of times can be identical or different, i.e. are independent of one another.

Accordingly, the invention in particular relates to those compounds of the formula I in which at least one of the radicals mentioned has one of the preferred meanings indicated above. Some preferred groups of compounds can be expressed by the following subformulae Ia to If, which correspond to the formula I and in which the radicals not designated in greater detail have the meanings indicated in the formula I, but in which in Ia X is $R^5$ substituted by COOH, COOA, $CONH_2$, $CONA_2$, CONHA or CN, or is phenyl or phenylmethyl;

in Ib $R^1$ and $R^2$ together are alkylene having 3–5 C atoms, —O—$CH_2$—$CH_2$—, —O—$CH_2$—O— or —O—$CH_2$—$CH_2$—O—, X is $R^5$ substituted by COOH, COOA, $CONH_2$, $CONA_2$, CONHA or CN, or is phenyl or phenylmethyl;

in Ic $R^1$, $R^2$ in each case independently of one another are H, A, OH, OA or Hal, $R^1$ and $R^2$ together are also alkylene having 3–5 C atoms, —O—$CH_2$—$CH_2$—, —O—$CH_2$—O— or —O—$CH_2$—$CH_2$—O—, X is $R^5$ substituted by COOH, COOA, $CONH_2$, $CONA_2$, CONHA or CN, or is phenyl or phenylmethyl;

in Id $R^1$, $R^2$ in each case independently of one another are H, A, OH, OA or Hal, $R^1$ and $R^2$ together are also alkylene having 3–5 C atoms, —O—$CH_2$—$CH_2$—, —O—$CH_2$—O— or —O—$CH_2$—$CH_2$—O—, X is alkylene having 2–5 C atoms, which is monosubstituted by $R^8$, or cyclohexyl, phenyl or phenylmethyl, $R^3$ is alkyl having 1–6 C atoms, $R^4$ is alkyl having 1–6 C atoms, $R^8$ is COOH or COOA, A is alkyl having 1 to 6 C atoms, Hal is F, Cl, Br or I;

in Ie $R^1$, $R^2$ in each case independently of one another are H, A, OH, OA or Hal, $R^1$ and $R^2$ together are also alkylene having 3–5 C atoms, —O—$CH_2$—$CH_2$—, —O—$CH_2$—O— or —O—$CH_2$—$CH_2$—O—, $R^3$ is alkyl having 1–6 C atoms, $R^4$ is alkyl having 1–6 C atoms, X is —$(CH_2)_{2-5}$—$R^8$, 4-$R^8$-cyclohexyl, 4-$R^8$-phenyl or 4-($R^8$-methyl)phenyl;

in If $R^1$, $R^2$ in each case independently of one another are H, A, OH, OA or Hal, $R^1$ and $R^2$ together are also alkylene having 3–5 C atoms, —O—$CH_2$—$CH_2$—, —O—$CH_2$—O— or —O—$CH_2$—$CH_2$—O—, $R^3$ is alkyl having 1–6 C atoms, $R^4$ is alkyl having 1–6 C atoms, X is —$(CH_2)_{2-5}$—$R^8$, in which one $CH_2$ group can be replaced by O, or is 4-$R^8$-cyclohexyl, 4-$R^8$-phenyl or 4-($R^8$-methyl)phenyl, $R^8$ is COOH or COOA.

The compounds of the formula I and also the starting substances for their preparation are otherwise prepared by methods known per se, such as are described in the literature (e.g. in the standard works such as Houben-Weyl, Methoden der organischen Chemie [Methods of organic chemistry], Georg-Thieme-Verlag, Stuttgart), namely under reaction conditions which are known and suitable for the reactions mentioned. In this case, use can also be made of variants which are known per se, but not mentioned here in greater detail.

In the compounds of the formula II or III, $R^1$, $R^2$, $R^3$, $R^4$ and X have the meanings indicated, in particular the preferred meanings indicated.

If L is a reactive esterified OH group, this is preferably alkylsulfonyloxy having 1–6 C atoms (preferably methylsulfonyloxy) or arylsulfonyloxy having 6–10 C atoms (preferably phenyl- or p-tolylsulfonyloxy, furthermore also 2-naphthalenesulfonyloxy).

The compounds of the formula I can preferably be obtained by reacting compounds of the formula II with compounds of the formula III.

If desired, the starting substances can also be formed in situ, such that they are not isolated from the reaction mixture but immediately reacted further to give the compounds of the formula I.

On the other hand, it is possible to carry out the reaction stepwise.

As a rule, the starting compounds of the formulae II and III are known. If they are not known, they can be prepared by methods known per se.

Compounds of the formula II can be prepared according to methods known from the literature, e.g. from 4-amino-3-alkoxycarbonylpyrazoles by cyclization with nitriles and subsequent reaction of the cyclization products with phosphorus oxychloride (analogous to Houben Weyl E9b/2).

In detail, the reaction of the compounds of the formula II with the compounds of the formula III is carried out in the presence or absence of an inert solvent at temperatures between approximately −20 and approximately 150°, preferably between 20 and 100°.

The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylamine, pyridine or quinoline or of an excess of the amine component can be favourable.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide, N-methylpyrrolidone or dimethylformamide (DMF); nitriles such as acetonitrile; sulfoxides such as dimethyl sulfoxide (DMSO); nitro compounds such as nitromethane or nitrobenzene; esters such as ethyl acetate or mixtures of the solvents mentioned.

It is furthermore possible to convert a radical X into another radical X in a compound of the formula I, e.g, by hydrolysing an ester or a cyano group to a COOH group.

Ester groups can be hydrolysed, for example, using NaOH or KOH in water, water/THF or water/dioxane at temperatures between 0 and 100°.

Carboxylic acids can be converted, for example, using thionyl chloride into the corresponding carbonyl chlorides and these can be converted into carboxamides. Carbonitriles are obtained from these in a known manner by dehydration.

An acid of the formula I can be converted into the associated acid addition salt using a base, for example by reaction of equivalent amounts of the acid and the base in an inert solvent such as ethanol and subsequent evaporation. Suitable bases for this reaction are those which yield physiologically acceptable salts.

Thus the acid of the formula I can be converted into the corresponding metal salts, in particular alkali metal or alkaline earth metal salts, or into the corresponding ammonium salt, using a base (e.g. sodium or potassium hydroxide or carbonate).

For this reaction, suitable organic bases are in particular also those which yield physiologically acceptable salts, such as, for example, ethanolamine.

On the other hand, a base of the formula I can be converted into the associated acid addition salt using an acid, for example by reaction of equivalent amounts of the base and of the acid in an inert solvent such as ethanol and subsequent evaporation. For this reaction, suitable acids are in particular those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene- mono- and -disulfonic acids and laurylsulfuric acid.

Salts with physiologically unacceptable acids, e.g. picrates, can be used for the isolation and/or purification of the compounds of the formula I.

The invention furthermore relates to the use of the compounds of the formula I and/or their physiologically acceptable salts for the production of pharmaceutical preparations, in particular by a non-chemical route. In this case, they can be brought into a suitable dose form together with at least one solid, liquid and/or semi-liquid vehicle or excipient and, if appropriate, in combination with one or more further active compounds.

The invention also relates to medicaments of the formula I and their physiologically acceptable salts as phosphodiesterase V inhibitors.

The invention furthermore relates to pharmaceutical preparations comprising at least one compound of the formula I and/or one of its physiologically acceptable salts.

These preparations can be used as medicaments in human or veterinary medicine. Possible vehicles are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc and petroleum jelly. In particular, tablets, pills, coated tablets, capsules, powders, granules, syrups, juices or drops are used for oral administration, suppositories are used for rectal administration, solutions, preferably oily or aqueous solutions, furthermore suspensions, emulsions or implants, are used for parenteral administration and ointments, creams or powders are used for topical application. The novel compounds can also be lyophilized and the lyophilizates obtained used, for example, for the production of injection preparations. The preparations indicated can be sterilized and/or can contain excipients such as lubricants, preservatives, stabilizers and/or wetting agents, emulsifiers, salts for affecting the osmotic pressure, buffer substances, colourants, flavourings and/or one or more further active compounds, e.g. one or more vitamins.

The compounds of the formula I and their physiologically acceptable salts can be used in the control of diseases in which an increase in the cGMP (cyclic guanosine monophosphate) level leads to inhibition or prevention of inflammation and muscle relaxation. The compounds according to the invention can particularly be used in the treatment of diseases of the cardiovascular system and for the treatment and/or therapy of potency disorders.

In this case, as a rule the substances are preferably administered in doses of between approximately 1 and 500 mg, in particular between 5 and 100 mg, per dose unit. The daily dose is preferably between approximately 0.02 and 10 mg/kg of body weight. The specific dose for each patient depends, however, on all sorts of factors, for example on the efficacy of the specific compound employed, on the age, body weight, general state of health, sex, on the diet, on the time and route of administration, on the excretion rate, pharmaceutical combination and severity of the particular disorder to which the therapy applies. Oral administration is preferred.

Above and below, all temperatures are indicated in ° C. In the following examples, "customary working up", means: if necessary, water is added, the mixture is adjusted, if necessary, depending on the constitution of the final product, to a pH of between 2 and 10 and extracted with ethyl acetate or dichloromethane, the organic phase is separated off, dried over sodium sulfate and evaporated, and the residue is purified by chromatography on silica gel and/or by crystallization.

Mass spectrometry (MS): EI (electron impact ionization) M⁺ FAB (fast atom bombardment) (M+H)⁺.

EXAMPLE 1

3 g of methyl 3-[7-chloro-1-methyl-3-propyl-1H-pyrazolo[4,3-d]pyrimidin-5-yl]propionate and 1.9 g of 3-chloro-4-methoxybenzylamine ("A") in 50 ml of dimethylformamide (DMF) are stirred at 60° for 12 hours in the presence of potassium carbonate. After filtration, the solvent is removed and the mixture is worked up in the customary manner. 4.6 g of methyl 3-[7-(3-chloro-4-methoxybenzylamino)-1-methyl-3-propyl-1H-pyrazolo[4,3-d]pyrimidin-5-yl]propionate are obtained as a colourless oil.

The following is obtained analogously by reaction of "A". with methyl 2-[7-chloro-1-methyl-3-propyl-1H-pyrazolo-[4,3-d]pyrimidin-5-yl]acetate methyl 2-[7-(3-chloro-4-methoxybenzylamino)-1-methyl-3-propyl-1H-pyrazolo[4,3-d]pyrimidin-5-yl] acetate.

The following is analogously obtained by reaction of 3,4-methylenedioxybenzylamine with methyl 3-[7-chloro-1-methyl-3-propyl-1H-pyrazolo-[4,3-d]pyrimidin-5-yl]propionate methyl 3-[7-(3,4-methylenedioxybenzylamino)-1-methyl-3-propyl-1H-pyrazolo[4,3-d]pyrimidin-5-yl] propionate.

The following is analogously obtained by reaction of "A". with methyl 4-[7-chloro-1-methyl-3-propyl-1H-pyrazolo-[4,3-d]pyrimidin-5-yl]butyrate methyl 4-[7-(3-chloro-4-methoxybenzylamino)-1-methyl-3-propyl-1H-pyrazolo[4,3-d]pyrimidin-5-yl] butyrate.

The following is analogously obtained by reaction of 3,4-methylenedioxybenzylamine with methyl 4-[7-chloro-1-methyl-3-propyl-1H-pyrazolo-[4,3-d]pyrimidin-5-yl]butyrate methyl 4-[7-(3,4-methylenedioxybenzylamino)-1-methyl-3-propyl-1H-pyrazolo[4,3-d]pyrimidin-5-yl] butyrate.

The following is analogously obtained by reaction of "A". with methyl 5-[7-chloro-1-methyl-3-propyl-1H-pyrazolo-[4,3-d]pyrimidin-5-yl]valerate methyl 5-[7-(3-chloro-4-methoxybenzylamino)-1-methyl-3-propyl-1H-pyrazolo[4,3-d]pyrimidin-5-yl] valerate.

The following is analogously obtained by reaction of 3,4-methylenedioxybenzylamine with methyl 5-[7-chloro-1-methyl-3-propyl-1H-pyrazolo-[4,3-d]pyrimidin-5-yl]valerate methyl 5-[7-(3,4-methylenedioxybenzylamino)-1-methyl-3-propyl-1H-pyrazolo[4,3-d]pyrimidin-5-yl] valerate.

The following is analogously obtained by reaction of "A". with methyl 7-[7-chloro-1-methyl-3-propyl-1H-pyrazolo-[4,3-d]pyrimidin-5-yl]heptanoate methyl 7-[7-(3-chloro-4-methoxybenzylamino)-1-methyl-3-propyl-1H-pyrazolo[4,3-d]pyrimidin-5-yl] heptanoate.

The following is analogously obtained by reaction of 3,4-methylenedioxybenzylamine with methyl 7-[7-chloro-1-methyl-3-propyl-1H-pyrazolo-[4,3-d]pyrimidin-5-yl]heptanoate methyl 7-[7-(3,4-methylenedioxybenzylamino)-1-methyl-3-propyl-1H-pyrazolo[4,3-d]pyrimidin-5-yl] heptanoate.

The following is analogously obtained by reaction of with methyl 2-[4-(7-chloro-1-methyl-3-propyl-1H-pyrazolo [4,3-d]pyrimidin-5-yl-)cyclohex-1-yl]acetate methyl 2-{4-[7-(3-chloro-4-methoxybenzylamino)-1-methyl-3-propyl-1H-pyrazolo[4,3-d]pyrimidin-5-yl] cyclohexyl-1-yl}acetate.

The following is analogously obtained by reaction of 3,4-methylenedioxybenzylamine with methyl 2-[4-(7-chloro-1-methyl-3-propyl-1H-pyrazolo [4,3-d]pyrimidin-5-yl]cyclohex-1-yl]acetate methyl 2-(4-[7-(3,4-methylenedioxybenzylamino)-1-methyl-3-propyl-1H-pyrazolo[4,3-d]pyrimidin-5-yl] cyclohexyl-1-yl}acetate.

The following are analogously obtained by reaction of benzylamine with methyl 3-[7-chloro-1-methyl-3-propyl-1H-pyrazolo-[4,3-d]pyrimidin-5-yl]propionate methyl 3-[7-benzylamino-1-methyl-3-propyl-1H-pyrazolo[4,3-d]pyrimidin-5-yl]propionate;

with methyl 4-[7-chloro-1-methyl-3-propyl-1H-pyrazolo-[4,3-d]pyrimidin-5-yl]butyrate methyl 4-[7-benzylamino-1-methyl-3-propyl-1H-pyrazolo[4,3-d]pyrimidin-5-yl]butyrate;

with methyl 5-[7-chloro-1-methyl-3-propyl-1H-pyrazolo-[4,3-d]pyrimidin-5-yl]valerate methyl 5-[7-benzylamino-1-methyl-3-propyl-1H-pyrazolo[4,3-d]pyrimidin-5-yl]valerate.

The following is analogously obtained by reaction of "A". with methyl 4-[7-chloro-1-methyl-3-propyl-1H-pyrazolo-[4,3-d]pyrimidin-5-yl]-cyclohexanecarboxylate methyl 4-[7-(3-chloro-4-methoxybenzylamino)-1-methyl-3-propyl-1H-pyrazolo[4,3-d]pyrimidin-5-yl] cyclohexanecarboxylate and the following is analogously obtained by reaction of 3,4-methylenedioxybenzylamine methyl 4-[7-(3,4-methylenedioxybenzylamino)-1-methyl-3-propyl-1H-pyrazolo[4,3-d]pyrimidin-5-yl] cyclohexanecarboxylate.

EXAMPLE 2

4.3 g of methyl 3-[7-(3-chloro-4-methoxybenzylamino)-1-methyl-3-propyl-1H-pyrazolo[4,3-d]pyrimidin-5-yl]-propionate are dissolved in 30 ml of tetrahydrofuran (THF) and, after addition of 10 ml of 10% NaOH, stirred at 60° for 8 hours. After addition of 10% HCl, the deposited crystals are separated off and recrystallized from methanol. 3.7 g of 3-[7-(3-chloro-4-methoxybenzylamino)-1-methyl-3-propyl-1H-pyrazolo[4,3-d]pyrimidin-5-yl]propionic acid, m.p. 178°, are obtained.

By evaporation with the equivalent amount of methanolic potassium hydroxide solution, the potassium salt of the acid is obtained as an amorphous powder.

Analogously, from the esters mentioned in Example 1, the compounds

2-[7-(3-chloro-4-methoxybenzylamino)-1-methyl-3-propyl-1H-pyrazolo[4,3-d]pyrimidin-5-yl]acetic acid, 3-[7-(3,4-methylenedioxybenzylamino)-1-methyl-3-propyl-1H-pyrazolo[4,3-d]pyrimidin-5-yl]propionic acid, 4-[7-(3-chloro-4-methoxybenzylamino)-1-methyl-3-propyl-1H-pyrazolo[4,3-d]pyrimidin-5-yl]butyric acid, m.p. 152°;

4-[7-(3,4-methylenedioxybenzylamino)-1-methyl-3-propyl-1H-pyrazolo[4,3-d]pyrimidin-5-yl]butyric acid, m.p. 172°;

5-[7-(3-chloro-4-methoxybenzylamino)-1-methyl-3-propyl-1H-pyrazolo[4,3-d]pyrimidin-5-yl]valeric acid, m.p. 159°;

5-[7-(3,4-methylenedioxybenzylamino)-1-methyl-3-propyl-1H-pyrazolo[4,3-d]pyrimidin-5-yl]valeric acid, ethanolamine salt, m.p. 160°;

7-[7-(3-chloro-4-methoxybenzylamino)-1-methyl-3-propyl-1H-pyrazolo[4,3-d]pyrimidin-5-yl]heptanoic acid, 7-[7-(3,4-methylenedioxybenzylamino)-1-methyl-3-propyl-1H-pyrazolo[4,3-d]pyrimidin-5-yl]heptanoic acid, 2-{4-[7-(3-chloro-4-methoxybenzylamino)-1-methyl-3-propyl-1H-pyrazolo[4,3-d]pyrimidin-5-yl]cyclohexyl-1-yl}acetic acid, 2-{4-[7-(3,4-methylenedioxybenzylamino)-1-methyl-3-propyl-1H-pyrazolo[4,3-d]pyrimidin-5-yl]cyclohexyl-1-yl}acetic acid, 3-[7-benzylamino-1-methyl-3-propyl-1H-pyrazolo-[4,3-d]pyrimidin-5-yl]propionic acid, 4-[7-benzylamino-1-methyl-3-propyl-1H-pyrazolo-[4,3-d]pyrimidin-5-yl]butyric acid, 5-[7-benzylamino-1-methyl-3-propyl-1H-pyrazolo-[4,3-d]pyrimidin-5-yl]valeric acid, m.p. 185°;

4-[7-(3-chloro-4-methoxybenzylamino)-1-methyl-3-propyl-1H-pyrazolo[4,3-d]pyrimidin-5-yl]cyclohexanecarboxylic acid, 4-[7-(3,4-methylenedioxybenzylamino)-1-methyl-3-propyl-1H-pyrazolo[4,3-d]pyrimidin-5-yl]cyclohexanecarboxylic acid, are obtained.

Analogously, the compounds

5-[7-(3-chloro-4-methoxybenzylamino)-1-methyl-3-isopropyl-1H-pyrazolo[4,3-d]pyrimidin-5-yl]valeric acid, cyclohexylamine salt, m.p. 148°;

4-[7-(3-chloro-4-methoxybenzylamino)-1-methyl-3-ethyl-1H-pyrazolo[4,3-d]pyrimidin-5-yl]butyric acid, m.p. 176°;

4-[7-(3,4-methylenedioxybenzylamino)-1-methyl-3-ethyl-1H-pyrazolo[4,3-d]pyrimidin-5-yl]butyric acid, m.p. 187°;

4-[7-(3-chloro-4-methoxybenzylamino)-1-ethyl-3-methyl-1H-pyrazolo[4,3-d]pyrimidin-5-yl]butyric acid, m.p. 206°;

4-[7-(3,4-methylenedioxybenzylamino)-1-ethyl-3-methyl-1H-pyrazolo[4,3-d]pyrimidin-5-yl]butyric acid, m.p. 177°;

4-[7-benzylamino-1-methyl-3-ethyl-1H-pyrazolo-[4,3-d]pyrimidin-5-yl]butyric acid, m.p. 208°;

4-[7-(3-chloro-4-methoxybenzylamino)-1-methyl-3-methyl-1H-pyrazolo[4,3-d]pyrimidin-5-yl]butyric acid, m.p. 250°;

4-[7-(3,4-methylenedioxybenzylamino)-1-methyl-3-methyl-1H-pyrazolo[4,3-d]pyrimidin-5-yl]butyric acid, m.p. 225°;

4-[7-benzylamino-1-methyl-3-methyl-1H-pyrazolo[4,3-d]pyrimidin-5-yl]butyric acid, m.p. 201°;

5-[7-(4-methoxybenzylamino)-1-methyl-3-propyl-1H-pyrazolo[4,3-d]pyrimidin-5-yl]valeric acid, m.p. 160°;

5-[7-(3-methoxybenzylamino)-1-methyl-3-propyl-1H-pyrazolo[4,3-d]pyrimidin-5-yl]valeric acid, m.p. 141°;

5-[7-(4-chlorobenzylamino)-1-methyl-3-propyl-1H-pyrazolo[4,3-d]pyrimidin-5-yl]valeric acid, m.p. 148°;

5-[7-(3-chlorobenzylamino)-1-methyl-3-propyl-1H-pyrazolo[4,3-d]pyrimidin-5-yl]valeric acid, m.p. 151°;

are obtained.

EXAMPLE 3

A mixture of 1.8 g of methyl 4-[7-chloro-1-methyl-3-propyl-1H-pyrazolo[4,3-d]pyrimidin-5-yl]phenylcarboxylate ("B") and 1.5 g of 3-chloro-4-methoxybenzylamine in 20 ml of N-methylpyrrolidone is heated at 110° for 4 hours. After cooling, it is worked up in the customary manner. 2.2 g of methyl 4-[7-(3-chloro-4-methoxybenzylamino)-1-methyl-3-propyl-1H-pyrazolo-[4,3-d]pyrimidin-5-yl]benzoate are obtained.

Analogously to Example 2, from 1.2 g of the ester, 1.0 g of

4-[7-(3-chloro-4-methoxybenzylamino)-1-methyl-3-propyl-1H-pyrazolo[4,3-d]pyrimidin-5-yl]benzoic acid, ethanolamine salt, m.p. 139° is obtained.

Analogously to Example 1, from "B" and 3,4-methylenedioxybenzylamine methyl 4-[7-(3,4-methylenedioxybenzylamino)-1-methyl-3-propyl-1H-pyrazolo[4,3-d]pyrimidin-5-yl]benzoate and, therefrom, by ester hydrolysis 4-[7-(3,4-methylenedioxybenzylamino)-1-methyl-3-propyl-1H-pyrazolo[4,3-d]pyrimidin-5-yl]benzoic acid are obtained.

Analogously, the compounds

4-[7-(3-chloro-4-methoxybenzylamino)-1-methyl-3-propyl-1H-pyrazolo[4,3-d]pyrimidin-5-yl]phenylacetic acid, glucamine salt, m.p. 114° and 4-[7-(3,4-methylenedioxybenzylamino)-1-methyl-3-propyl-1H-pyrazolo[4,3-d]pyrimidin-5-yl]phenylacetic acid are obtained.

EXAMPLE 4

1 equivalent of 3-[7-(3-chloro-4-methoxybenzylamino)-1-methyl-3-propyl-1H-pyrazolo[4,3-d]pyrimidin-5-yl]-propionic acid and 1.2 equivalents of thionyl chloride are stirred in dichloromethane for 2 hours. The solvent is removed and 3-[7-(3-chloro-4-methoxybenzylamino)-1-methyl-3-propyl-1H-pyrazolo[4,3-d]pyrimidin-5-yl]-propionyl chloride is obtained. The product is transferred to aqueous ammonia, stirred for one hour and, after customary working up, 3-[7-(3-chloro-4-methoxybenzylamino)-1-methyl-3-propyl-1H-pyrazolo[4,3-d]-pyrimidin-5-yl]propionamide is obtained.

EXAMPLE 5

1 equivalent of DMF and 1 equivalent of oxalyl chloride are dissolved in acetonitrile at 0°. 1 equivalent of 3-[7-(3-chloro-4-methoxybenzylamino)-1-methyl-3-propyl-1H-pyrazolo[4,3-d]pyrimidin-5-yl]propionamide is then added. The mixture is stirred for one hour. After customary working up, 3-[7-(3-chloro-4-methoxybenzylamino)-1-methyl-3-propyl-1H-pyrazolo[4,3-d]-pyrimidin-5-yl]propionitrile is obtained.

EXAMPLE 6

Analogously to Examples 1, 2 and 3, by reaction of the corresponding chloropyrimidine derivatives with 3,4-ethylenedioxybenzylamine, the carboxylic acids below are obtained 4-[7-(3,4-ethylenedioxybenzylamino)-1-methyl-3-propyl-1H-pyrazolo[4,3-d]pyrimidin-5-yl]butyric acid, 3-[7-(3,4-ethylenedioxybenzylamino)-1-methyl-3-propyl-1H-pyrazolo[4,3-d]pyrimidin-5-yl]propionic acid, 5-[7-(3,4-ethylenedioxybenzylamino)-1-methyl-3-propyl-1H-pyrazolo[4,3-d]pyrimidin-5-yl]valeric acid, 7-[7-(3,4-ethylenedioxybenzylamino)-1-methyl-3-propyl-1H-pyrazolo[4,3-d]pyrimidin-5-yl]heptanoic acid, 2-{4-[7-(3,4-ethylenedioxybenzylamino)-1-methyl-3-propyl-1H-pyrazolo[4,3-d]pyrimidin-5-yl]cyclohexyl-1-yl}acetic acid, 4-[7-(3,4-ethylenedioxybenzylamino)-1-methyl-3-propyl-1H-pyrazolo[4,3-d]pyrimidin-5-yl]cyclohexanecarboxylic acid, 4-[7-(3,4-ethylenedioxybenzylamino)-1-methyl-3-propyl-1H-pyrazolo[4,3-d]pyrimidin-5-yl]benzoic acid, 4-[7-(3,4-ethylenedioxybenzylamino)-1-methyl-3-propyl-1H-pyrazolo[4,3-d]pyrimidin-5-yl]benzoic acid, 4-[7-(3,4-ethylenedioxybenzylamino)-1-methyl-3-propyl-1H-pyrazolo[4,3-d]pyrimidin-5-yl]phenylacetic acid.

Analogously, by reaction with 3,4-dichlorobenzylamine the compounds below

4-[7-(3,4-dichlorobenzylamino)-1-methyl-3-propyl-1H-pyrazolo[4,3-d]pyrimidin-5-yl]butyric acid, m.p. 209°, 3-[7-(3,4-dichlorobenzylamino)-1-methyl-3-propyl-1H-pyrazolo[4,3-d]pyrimidin-5-yl]propionic acid, 5-[7-(3,4-dichlorobenzylamino)-1-methyl-3-propyl-1H-pyrazolo[4,3-d]pyrimidin-5-yl]valeric acid, 7-[7-(3,4-dichlorobenzylamino)-1-methyl-3-propyl-1H-pyrazolo[4,3-d]pyrimidin-5-yl]heptanoic acid, 2-{4-[7-(3,4-dichlorobenzylamino)-1-methyl-3-propyl-1H-pyrazolo[4,3-d]pyrimidin-5-yl]cyclohexyl-1-yl}acetic acid, 4-[7-(3,4-dichlorobenzylamino)-1-methyl-3-propyl-1H-pyrazolo[4,3-d]pyrimidin-5-yl]cyclohexanecarboxylic acid, 4-[7-(3,4-dichlorobenzylamino)-1-methyl-3-propyl-1H-pyrazolo[4,3-d]pyrimidin-5-yl]benzoic acid, 4-[7-(3,4-dichlorobenzylamino)-1-methyl-3-propyl-1H-pyrazolo[4,3-d]pyrimidin-5-yl]phenylacetic acid, are obtained.

Analogously, by reaction with 3-chloro-4-ethoxybenzylamine the compounds below

4-[7-(3-chloro-4-ethoxybenzylamino)-1-methyl-3-propyl-1H-pyrazolo[4,3-d]pyrimidin-5-yl]butyric acid, 3-[7-(3-chloro-4-ethoxybenzylamino)-1-methyl-3-propyl-1H-pyrazolo[4,3-d]pyrimidin-5-yl]propionic acid, 5-[7-(3-chloro-4-ethoxybenzylamino)-1-methyl-3-propyl-1H-pyrazolo[4,3-d]pyrimidin-5-yl]valeric acid, 7-[7-(3-chloro-4-ethoxybenzylamino)-1-methyl-3-propyl-1H-pyrazolo[4,3-d]pyrimidin-5-yl]heptanoic acid, 2-{4-[7-(3-chloro-4-ethoxybenzylamino)-1-methyl-3-propyl-1H-pyrazolo[4,3-d]pyrimidin-5-yl]cyclohexyl-1-yl}acetic acid, 4-[7-(3-chloro-4-ethoxybenzylamino)-1-methyl-3-propyl-1H-pyrazolo[4,3-d]pyrimidin-5-yl]cyclohexanecarboxylic acid, 4-[7-(3-chloro-4-ethoxybenzylamino)-1-methyl-3-propyl-1H-pyrazolo[4,3-d]pyrimidin-5-yl]benzoic acid, 4-[7-(3-chloro-4-ethoxybenzylamino)-1-methyl-3-propyl-1H-pyrazolo[4,3-d]pyrimidin-5-yl]phenylacetic acid, are obtained.

Analogously, by reaction with 3-chloro-4-isopropoxybenzylamine the compounds below 4-[7-(3-chloro-4-isopropoxybenzylamino)-1-methyl-3-propyl-1H-pyrazolo[4,3-d]pyrimidin-5-yl]butyric acid, 3-[7-(3-chloro-4-isopropoxybenzylamino)-1-methyl-3-propyl-1H-pyrazolo[4,3-d]pyrimidin-5-yl]propionic acid, 5-[7-(3-chloro-4-isopropoxybenzylamino)-1-methyl-3-propyl-1H-pyrazolo[4,3-d]pyrimidin-5-yl]valeric acid, 7-[7-(3-chloro-4-isopropoxybenzylamino)-1-methyl-3-propyl-1H-pyrazolo[4,3-d]pyrimidin-5-yl]heptanoic acid, 2-{4-[7-(3-chloro-4-isopropoxybenzylamino)-1-methyl-3-propyl-1H-pyrazolo[4,3-d]pyrimidin-5-yl]cyclohexyl-1-yl}acetic acid, 4-[7-(3-chloro-4-isopropoxybenzylamino)-1-methyl-3-propyl-1H-pyrazolo[4,3-d]pyrimidin-5-yl]cyclohexanecarboxylic acid, 4-[7-(3-chloro-4-isopropoxybenzylamino)-1-methyl-3-propyl-1H-pyrazolo[4,3-d]pyrimidin-5-yl]benzoic acid, 4-[7-(3-chloro-4-isopropoxybenzylamino)-1-methyl-3-propyl-1H-pyrazolo[4,3-d]pyrimidin-5-yl]phenylacetic acid, are obtained.

EXAMPLE 7

Analogously to Examples 1 and 2, the compound
[7-(3-chloro-4-methoxybenzylamino)-1-methyl-3-propyl-1H-pyrazolo[4,3-d]pyrimidin-5-ylmethoxy]acetic acid, ethanolamine salt, m.p. 138°,
is obtained.

The following examples relate to pharmaceutical preparations:

Example A: Injection Vials

A solution of 100 g of an active compound of the formula I and 5 g of disodium hydrogenphosphate is adjusted to pH 6.5 in 3 l of double-distilled water using 2 N hydrochloric acid, sterile filtered, dispensed into injection vials, lyophilized under sterile conditions and aseptically sealed. Each injection vial contains 5 mg of active compound.

Example B: Suppositories

A mixture of 20 g of active compound of the formula I is fused with 100 g of soya lecithin and 1400 g of cocoa butter, poured into moulds and allowed to cool. Each suppository contains 20 mg of active compound.

Example C: Solution

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water. It is adjusted to pH 6.8, made up to 1 and sterilized by irradiation. This solution can be used in the form of eye drops.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F: Coated Tablets

Analogously to Example E, tablets are pressed and are then coated in a customary manner with a coating of sucrose, potato starch, talc, tragacanth and colourant.

Example G: Capsules 2 kg of active compound of the formula I are dispensed in a customary manner into hard gelatin capsules such that each capsule contains 20 mg of the active compound.

Example H: Ampoules

A solution of 1 kg of active compound of the formula I in 60 l of double-distilled water is sterile filtered, dispensed in ampoules, lyophilized under sterile conditions and aseptically sealed. Each ampoule contains 10 mg of active compound.

Example I: Inhalation Spray 14 g of active compound of the formula I are dissolved in 10 l of isotonic NaCl solution and the solution is filled into commercially available spray containers having a pump mechanism. The solution can be sprayed into the mouth or nose. One puff of spray (approximately 0.1 ml) corresponds to a dose of approximately 0.14 mg.

What is claimed is:

1. A compound of the formula I

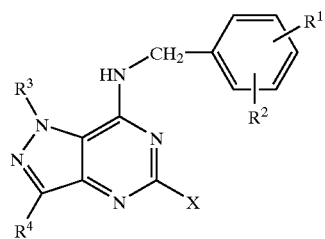

in which
  $R^1$ and $R^2$ are each, independently of one another, H, A, OH, OA or Hal,
  $R^1$ and $R^2$ together are alternatively alkylene having 3–5 carbon atoms, —O—CH$_2$—CH$_2$—, —CH$_2$—O—CH$_2$—, —O—CH$_2$—O— or —O—CH$_2$—CH$_2$—O—,
  $R^3$ and $R^4$ are each, independently of one another, H or A,
  X is $R^5$, $R^6$ or $R^7$ monosubstituted by $R^8$,
  $R^5$ is linear or branched alkylene having 1–10 carbon atoms, in which one or two CH$_2$ groups are optionally replaced by —CH=CH— groups, O, S or SO,
  $R^6$ is cycloalkyl or cycloalkylalkylene having 5–12 carbon atoms,
  $R^7$ is phenyl or phenylmethyl,
  $R^8$ is COOH, COOA, CONH$_2$, CONHA, CON(A)$_2$ or CN,
  A is alkyl having from 1 to 6 carbon atoms, and
  Hal is F, Cl, Br or I,
or a physiologically acceptable salt thereof.

2. A compound of the formula I according to claim 1 that is selected from the group consisting of
  (a) 5-[7-(3-chloro-4-methoxybenzylamino)-1-methyl-3-propyl-1H-pyrazolo[4,3-d]pyrimidin-5-yl]pentanoic acid;
  (b) 4-[7-(3-chloro-4-methoxybenzylamino)-1-methyl-3-propyl-1H-pyrazolo[4,3-d]pyrimidin-5-yl]benzoic acid;
  (c) 4-[7-(3,4-methylenedioxybenzylamino)-1-methyl-3-propyl-1H-pyrazolo[4,3-d]pyrimidin-5-yl]butyric acid;
  (d) 5-[7-(benzylamino)-1-methyl-3-propyl-1H-pyrazolo[4,3-d]pyrimidin-5-yl]pentanoic acid;
  (e) [7-(3-chloro-4-methoxybenzylamino)-1-methyl-3-propyl-1H-pyrazolo[4,3-]pyrimidin-5-ylmethoxy]acetic acid;
and a physiologically acceptable salt thereof.

3. A process for preparing a compound of the formula I according to claim 1 or a salt thereof, comprising
  a) reacting a compound of the formula II

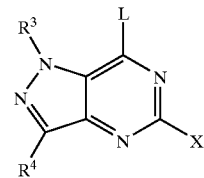

in which
    $R^3$, $R^4$ and X are as defined in claim 1,
    and L is Cl, Br, OH, SCH$_3$ or a reactive esterified OH group,
  with a compound of the formula III

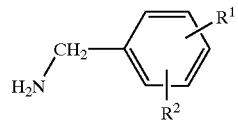

in which
    $R^1$ and $R^2$ are as defined above, or
  b) converting a radical X in a compound of the formula I into another radical X by hydrolysing an ester group to a COOH group or converting a COOH group into an amide or into a cyano group and/or converting a compound of the formula I into one of its salts.

4. A pharmaceutical composition, comprising at least one compound of the formula I according to claim 1 and/or a physiologically acceptable salt thereof and a pharmaceutically acceptable carrier.

5. A method of preparing a pharmaceutical composition comprising bringing together a compound according to claim 1 and a pharmaceutically acceptable carrier.

6. A method of treating a potency disorder, comprising administering a compound of claim 1 to a patient in need thereof.

7. A method of treating cardiac insufficiency, comprising administering a compound of claim 1 to a patient in need thereof.

8. A method of treating erectile dysfunction, comprising administering a compound of claim 1 to a patient in need thereof.

9. A compound of the formula I according to claim 1, wherein X is $R^5$ monosubstituted by $R^8$.

10. A compound of the formula I according to claim 1, wherein $R^1$ and $R^2$ together are alkylene having 3–5 C atoms, —O—$CH_2$—$CH_2$—, —O—$CH_2$—O— or —O—$CH_2$—$CH_2$—O—, and X is $R^5$ substituted by $R^8$.

11. A compound of the formula I according to claim 1, wherein $R^1$, $R^2$, in each case independently of one another, are H, A, OH, OA or Hal, or $R^1$ and $R^2$ together are alkylene having 3–5 C atoms, —O—$CH_2$—$CH_2$—, —O—$CH_2$—O— or —O—$CH_2$—$CH_2$—O—, and X is $R^5$ monosubstituted by $R^8$.

12. A compound of the formula I according to claim 1, wherein $R^1$, $R^2$, in each case independently of one another, are H, A, OH, OA or Hal, or $R^1$ and $R^2$ together are alkylene having 3–5 C atoms, —O—$CH_2$—$CH_2$—, —O—$CH_2$—O— or —O—$CH_2$—$CH_2$—O—, and X is alkylene having 2–5 C atoms, which is monosubstituted by $R^8$, $R^3$ is alkyl having 1–6 C atoms, $R^4$ is alkyl having 1–6 C atoms, $R^8$ is COOH or COOA, A is alkyl having 1 to 6 C atoms, and Hal is F, Cl, Br or I.

13. A compound of the formula I according to claim 1, wherein $R^1$, $R^2$, in each case independently of one another are H, A, OH, OA or Hal, or $R^1$ and $R^2$, together are alkylene having 3–5 C atoms, —O—$CH_2$—$CH_2$—, —O—$CH_2$—O— or —O—$CH_2$—$CH_2$—O—, $R^3$ is alkyl having 1–6 C atoms, $R^4$ is alkyl having 1–6 C atoms, and X is —$(CH_2)_{2-5}$—$R^8$, 4-$R^8$-cyclohexyl, 4-$R^8$-phenyl or 4-($R^8$-methyl)phenyl.

14. A compound of the formula I according to claim 1, wherein $R^1$, $R^2$, in each case independently of one another are H, A, OH, OA or Hal, $R^1$ and $R^2$ together are also alkylene having 3–5 C atoms, —O—$CH_2$—$CH_2$—, —O—$CH_2$—O— or —O—$CH_2$—$CH_2$—O—, $R^3$ is alkyl having 1–6 C atoms, $R^4$ is alkyl having 1–6 C atoms, X is —$(CH_2)_{2-5}$—$R^8$, in which one $CH_2$ group is optionally replaced by O, or is 4-$R^8$-cyclohexyl, 4-$R^8$-phenyl or 4-($R^8$-methyl)phenyl, and $R^8$ is COOH or COOA.

15. A compound of the formula I according to claim 1, wherein $R^5$ is ethylene, propylene, butylene or $CH_2$—O—$CH_2$.

16. A compound of the formula I according to claim 1, wherein $R^8$ COOH or COOA.

* * * * *

UNITED STATES PATENT AND TRADEMARK OFFICE
CERTIFICATE OF CORRECTION

PATENT NO. : 6,777,419 B1
DATED : August 17, 2004
INVENTOR(S) : Jonas et al.

It is certified that error appears in the above-identified patent and that said Letters Patent is hereby corrected as shown below:

Column 14,
Line 14, "[4,3-]" should be -- [4,3-d] --.

Signed and Sealed this

Twelfth Day of April, 2005

JON W. DUDAS
*Director of the United States Patent and Trademark Office*